US012733924B2

(12) United States Patent
Linden et al.

(10) Patent No.: US 12,733,924 B2
(45) Date of Patent: Sep. 15, 2026

(54) SUTURE DEVICE

(71) Applicant: Arthrex, Inc., Naples, FL (US)

(72) Inventors: David John Linden, North Yorkshire (GB); Matthew John Ravenscroft, Cheshire (GB); Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 574 days.

(21) Appl. No.: 17/996,509

(22) PCT Filed: Mar. 29, 2021

(86) PCT No.: PCT/US2021/024611
§ 371 (c)(1),
(2) Date: Oct. 19, 2022

(87) PCT Pub. No.: WO2021/257149
PCT Pub. Date: Dec. 23, 2021

(65) Prior Publication Data

US 2023/0099945 A1 Mar. 30, 2023

(30) Foreign Application Priority Data

Jun. 16, 2020 (EP) .................................... 20180257

(51) Int. Cl.
*A61B 17/06* (2006.01)
*D03D 1/00* (2006.01)
(Continued)

(52) U.S. Cl.
CPC ......... *A61B 17/06166* (2013.01); *D03D 1/00* (2013.01); *D03D 3/005* (2013.01);
(Continued)

(58) Field of Classification Search
CPC ...................... A61B 17/06166; D10B 2509/04
See application file for complete search history.

(56) References Cited

U.S. PATENT DOCUMENTS 4,530,113 A 7/1985 Matterson
4,668,233 A * 5/1987 Seedhom ........... A61B 17/1714 623/13.11

(Continued)

FOREIGN PATENT DOCUMENTS

CN 102271620 A 12/2011
EP 0126520 A2 11/1984

(Continued)

OTHER PUBLICATIONS

"Leno Weave" https://www2.cs.arizona.edu/patterns/weaving/monographs/ics512.pdf (Year: 2003).*

(Continued)

*Primary Examiner* — Erin Mcgrath
(74) *Attorney, Agent, or Firm* — Potomac Law Group, PLLC

(57) ABSTRACT

A suture device comprises at least one weft strand interwoven with a plurality of warp strands to define a body region. The body region has a substantially open mesh construction and at least a first elongate end region axially extending from and being one part with the body region having a substantially closed mesh construction. The width of the end region is substantially less than a width of the body region.

14 Claims, 15 Drawing Sheets

(51) Int. Cl.
*D03D 3/00* (2006.01)
*D03D 9/00* (2006.01)
*A61B 17/00* (2006.01)

(52) U.S. Cl.
CPC ...... *D03D 9/00* (2013.01); *A61B 2017/00526* (2013.01); *A61B 2017/06185* (2013.01); *D10B 2509/04* (2013.01)

(56) References Cited

U.S. PATENT DOCUMENTS

| | | | | |
|---|---|---|---|---|
| 2008/0188936 | A1 | 8/2008 | Ball et al. | |
| 2010/0063599 | A1* | 3/2010 | Brunelle | A61L 31/041 623/23.72 |
| 2011/0054524 | A1* | 3/2011 | Beevers | A61F 2/08 606/228 |
| 2012/0171917 | A1 | 7/2012 | Rasmussen et al. | |
| 2019/0374337 | A1 | 12/2019 | Zamani et al. | |
| 2020/0170779 | A1 | 6/2020 | Tascan et al. | |

FOREIGN PATENT DOCUMENTS

| | | | |
|---|---|---|---|
| EP | 0744165 | A1 | 11/1996 |
| EP | 1520552 | B1 | 7/2008 |
| EP | 2387970 | A1 | 11/2011 |
| GB | 2474866 | A | 5/2011 |
| WO | 2001080788 | A2 | 11/2001 |
| WO | 2009109778 | A2 | 9/2009 |
| WO | 2012121986 | A2 | 9/2012 |

OTHER PUBLICATIONS

International Search Report and Written Opinion dated Dec. 14, 2021, issued in International Application No. PCT/US2021/024611.

Invitation to Pay Additional Fee And, Where Applicable, Protest Fee dated Aug. 31, 2021, issued in International Application No. PCT/US2021/024611.

Office Action for Australian Patent Application No. 2021293512 issued on Aug. 1, 2024.

Office Action issued in CN Pat. Appln. No. 202180042773.4 issued Sep. 2, 2025.

* cited by examiner 250
252
200
250
202
252
208
204

1103
1152
1102
1101
1105
1106

1104
1103
1152
1101
1102
1105
1106

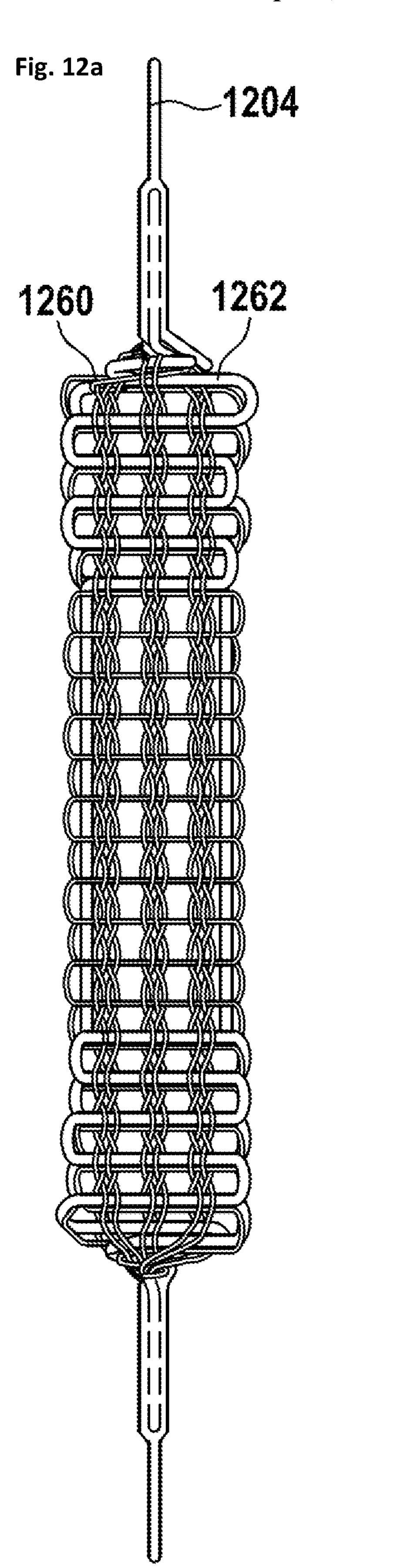
Fig. 12a
1204
1260
1262
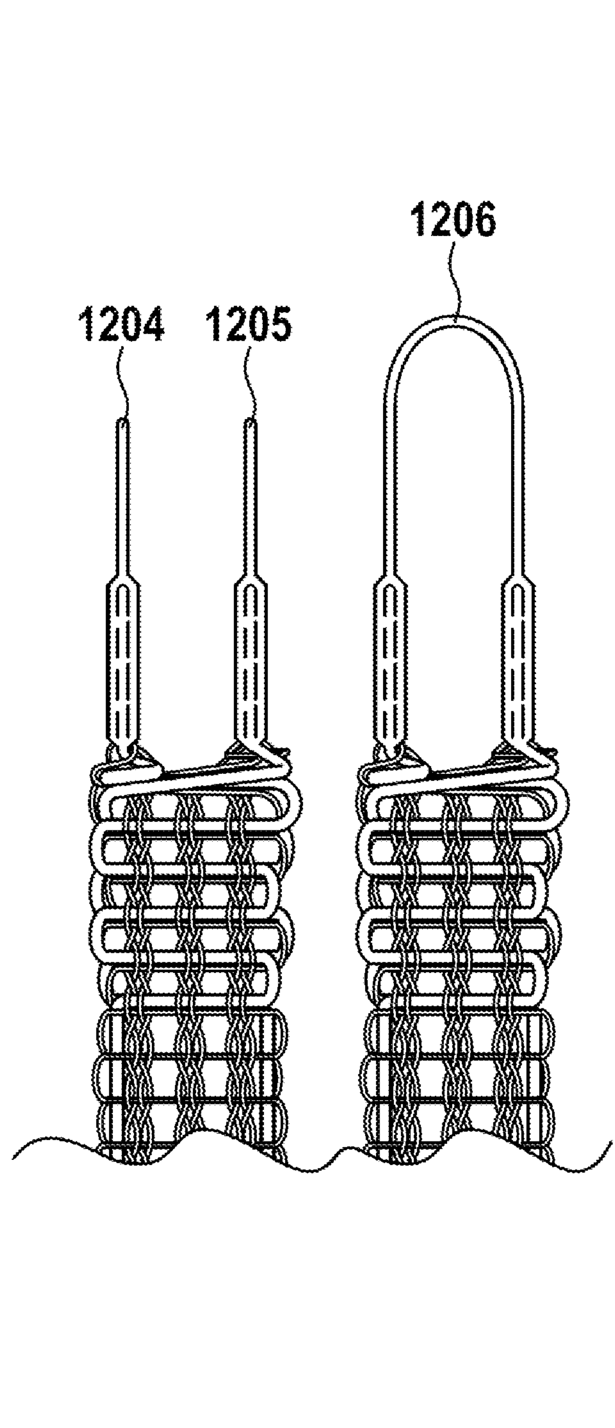
Fig. 12b
Fig. 12c
1206
1204
1205

1300
1352
1350

SUTURE DEVICE

This application is a U.S. national stage filing under 35 U.S.C. § 371 of International Application No. PCT/US2021/024611 filed Mar. 29, 2021, which claims priority to and the benefit of European Patent Application No. 20180257.6 filed Jun. 16, 2020, all of which are hereby incorporated by reference in their entireties.

FIELD OF THE INVENTION

The invention relates to a medical device which may be a suture device for orthopedic repairs, such as to reattach muscle or ligament to the tissue from which it has become detached, to anchor grafts and prosthetic devices to underlying tissue, or to reconstruct damaged or torn tissue.

DESCRIPTION OF THE RELATED ART

Conventional surgical techniques require the use of a suture to engage with soft tissue such as a tendon or ligament, or hard tissue such as bone. A suture is typically constructed with a relatively small diameter which results in a small contact area and high contact forces which may cause it to cut into the adjacent tissue.

SUMMARY

The problem to be solved is to provide an enhanced suture tape having a flatter and wider profile, and providing improved utility for a range of surgical applications, whilst allowing use with existing instrumentation, improved contact pressure during the surgical repair, and the ability to integrate with adjacent tissue.

Solutions of the problem are described in the independent claims. The dependent claims relate to further improvements.

In a first embodiment there is provided a suture device including at least one weft strand interwoven with a plurality of warp strands to define a body region having a substantially open mesh construction and at least a first elongate end region axially extending from and being one part with the body region having a substantially closed mesh construction and a width substantially less than a width of the body portion. The suture device may include a body region located between an adjacent first end region and an optional second end region. The construction of the body region may provide resistance to tissue pull-through and the construction of the adjacent end regions allow the device to be manipulated during surgical procedures.

Generally, an open mesh construction has a larger pore size than a closed mesh construction. A pore size may be defined by the maximum opening between adjacent weft and warp strands. An average pore size is defined as an average value of multiple pore sizes of the same pore type. An open mesh construction may be characterized in that the average pore size, or substantially each pore size, is at least 100 μm which may to allow cellular nutrition while supporting cell migration and proliferation resulting in tissue repair. A target pore size may be 0.3 mm or 0.5 mm. The pore size may be less than 1 or 2 mm.

A closed mesh construction may be characterized in that the average pore size, or substantially each pore size, is less than 100 μm which may allow to pack the textile fabric into a compressed dimension to support its use with existing surgical instrumentation.

The body region and the at least one end region may include a textile fabric. A textile fabric is intended to include a selection of constructions, interlaced and non-interlaced, whether made by braiding, weaving, knitting, crocheting, plaiting, twisting, plying, embroidery, bonding, laminating, non-woven or other processes and combinations thereof. The textile constructions may be fabricated from strands. The term ‘strands’ is intended to include fiber, monofilament, multi-filament yarns that may or may not be twisted, textile constructions such as braids, or a combination of these. Strands may have uniform or varying shape or size. Strands may consist of uniform material, or a combination of various materials. The discrete strands may include the same material or different materials. Variations between strands in terms of construction, shape, size, material, coating, or mechanical properties, may be equally geometrically arranged, or irregularly spaced.

The device may include a plurality of interwoven strands comprising a plurality of warps, which may be aligned substantially parallel with the longitudinal axis. It may further include a plurality of wefts which may be aligned substantially transverse to the longitudinal axis. The wefts may be provided by a single weft strand extending through the warps. The weft strand may extend substantially perpendicularly back and forth across the device with respect to a longitudinal axis thereof and partially along the edge portions of the device substantially parallel with the longitudinal axis of the device. The weft strand may be thicker than the warp strands. The weft may substantially be hollow. The warps may be arranged in adjacent pairs and may be interwoven with the weft strand to create a leno-weave construction which is also known as a gauze weave or cross weave. The strands may include twisted fibers. A leno weave may include at least two warp strands twisted in a series of figure eights around at least one weft strand, wherein a first warp strand passes under the weft strand and over a second warp strand and the second warp strand passes over the weft strand.

In an embodiment, the device includes a second elongate end region axially extending from the body region in an opposed direction to the first end region and being one part with the body region.

Further, the device may include a tapered transition region defined between and being one part with the body region and/or end regions.

In an embodiment, the plurality of warp strands includes sets of at least two warp strands.

In an embodiment, the sets of warp strands may include groups of adjacent pairs of warp strands.

In an embodiment, a first warp strand of the sets of warp strands is substantially planar and a second warp strand of the sets is interwoven with the at least one weft strand.

In an embodiment, a set of warp strands includes a greater number of said first warp strands than said second warp strands.

In an embodiment, a thickness of said first warp strand is greater than a thickness of said second warp strand.

In an embodiment, the sets of warp strands of the body region are substantially parallel and spaced apart to define the open mesh construction.

In an embodiment, the at least one weft strand extending through at least a portion of the body region and/or at least a portion of the at least one end region includes a plurality of weft strands.

In an embodiment, at least one end portion of the body region includes the plurality of weft strands whereas a central portion of the body region includes a single weft strand.

In an embodiment, both end portions of the body region include the plurality of weft strands.

In an embodiment, at least one of the weft strands of the at least one end portion of the body region are relatively stiff whereas the weft strand of the central portion of the body region is relatively flexible.

In an embodiment, the relatively stiff weft strand includes a braided cord and the relatively flexible weft strand includes at least one filament.

In an embodiment, a first weft strand of the plurality of weft strands is thicker than a second weft strand of the plurality of weft strands.

In an embodiment, the at least one weft strand extends substantially longitudinally from a portion of the body region.

In an embodiment, the at least one weft strand extends substantially along at least one edge of a central portion of the body region.

In an embodiment, the at least one weft strand extends substantially along opposed edges of a central portion of the body region.

In an embodiment, each weft yarn is running through separate eyes of the warp.

In an embodiment, the at least one weft strand of the at least one end region includes at least one corded construction.

In an embodiment, at least an end portion of the at least one corded construction is substantially hollow.

In an embodiment, free ends of the warp strands of the at least one end region are located inside the at least one corded construction by one or more splices to define at least one corded end region.

In an embodiment, at least one weft strand is provided by a corded construction.

In an embodiment, at least one warp strand is provided by a corded construction.

In an embodiment, a first portion of the free ends of the warp strands of the at least one end region are located inside a first corded construction by one or more splices to define a first corded end region and a second portion of the free ends of the warp strands of the at least one end region are located inside a second corded construction by one or more splices to define a second corded end region.

In an embodiment, the first and second corded end regions are connected to form at least one looped end region.

In an embodiment, the at least one looped end region is adjustable in length by passing at least the first corded end region within the second corded end region.

In an embodiment, the at least one looped end region is adjustable in length by passing at least one of the first and second corded end regions within itself.

In an embodiment, one or more fixation buttons are attached to the at least one looped end region.

In an embodiment, the body region is substantially planar or tubular.

According to another embodiment, a method of manufacturing a suture device is provided. The method including the steps of:

interweaving at least one weft strand with a plurality of warp strands to define a substantially open mesh construction; and applying a tension to the at least one weft strand to urge the warp strands together and define a body region having a substantially open mesh construction and at least a first elongate end region axially extending from and being one part with the body region having a substantially closed mesh construction and a width substantially less than a width of the body portion.

In an embodiment, the method includes providing a tapered transition region between and being one part with the body region and/or an end region.

In an embodiment, the method includes providing sets of at least two warp strands wherein a first warp strand of a set of warp strands is substantially planar and a second warp strand of a set is interwoven with the at least one weft strand.

In an embodiment, a thickness of said first warp strand is greater than a thickness of said second warp strand.

In an embodiment, interweaving includes extending a plurality of weft strands through at least a portion of the body region and/or at least a portion of the at least one end region.

In an embodiment, the method includes locating free ends of the warp strands of the at least one end region inside a corded and hollow construction of the at least one weft strand by one or more splices to define at least one corded end region.

In an embodiment, the method includes locating free ends of the warp strands of the at least one end region inside a corded and hollow construction of the at least one warp strand by one or more splices to define at least one corded end region.

In an embodiment, the method includes cutting the at least one end region proximal the urged together warp strands.

In an embodiment, the method includes binding free ends of the warp strands and/or the at least one weft strand together.

DESCRIPTION OF DRAWINGS

In the following the invention will be described by way of example, without limitation of the general inventive concept, on examples of embodiment with reference to the drawings.

FIG. 12*a* illustrates the construction of a tenth suture;

FIG. 12*b* illustrates the construction of an eleventh suture;

FIG. 12*c* illustrates the construction of a twelfth suture;

DETAILED DESCRIPTION

Figure 1:
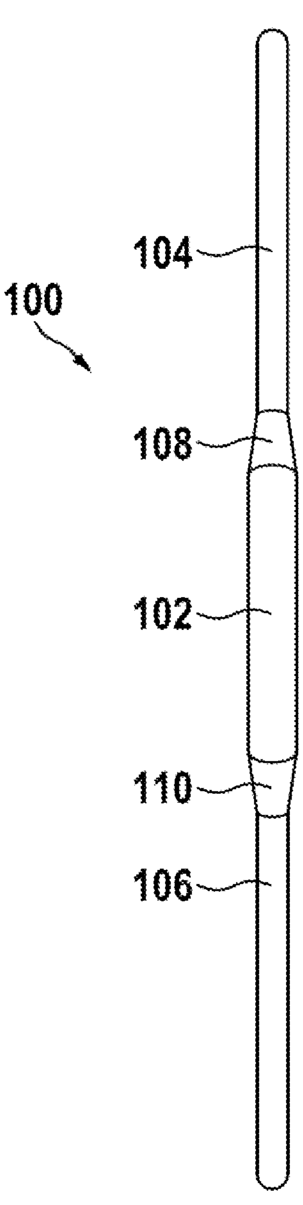
FIG. 1 illustrates a suture.

As illustrated in FIG. 1, a surgical suture device 100 according to an embodiment includes a continuous length of suture material. The suture material has one or more regions of defined construction. The device includes a body region 102 located between an adjacent first end region 104 and an optional second end region 106. The construction of the body region provides resistance to tissue pull-through and the construction of the adjacent end regions allow the device to be manipulated during surgical procedures. The body region may have a substantially flat, circular, or tubular profile. It may be fabricated from sheet, a textile fabric, or a combination of these constructions. Provided between an end region and the body region is a tapered transition region 108,110.

Aptly, the body region 102 and the at least one end region 104,106 include a textile fabric. A textile fabric may include a selection of constructions, interlaced and non-interlaced, whether made by braiding, weaving, knitting, crocheting, plaiting, twisting, plying, embroidery, bonding, laminating, non-woven or other processes and combinations thereof. The textile constructions may be fabricated from strands. The term 'strands' is intended to include fiber, monofilament, multi-filament yarns that may or may not be twisted, textile constructions such as braids, or a combination of these. Strands may have uniform or varying shape or size. Strands may consist of uniform material, or a combination of various materials. The discrete strands may be the same material or different materials. Variations between strands in terms of construction, shape, size, material, coating, or mechanical properties, may be equally geometrically arranged, or irregularly spaced.

Figures 2A, 2B:
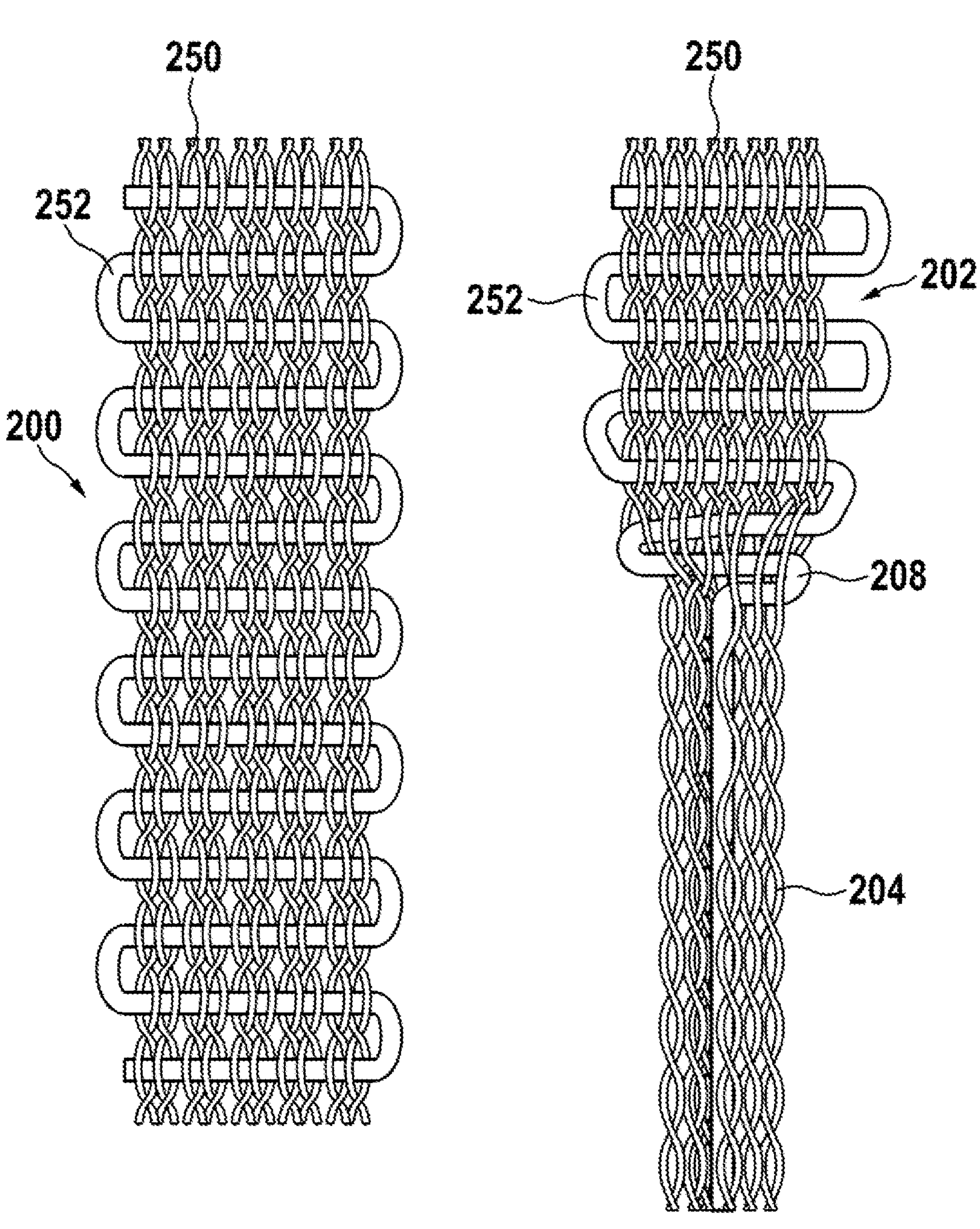
FIG. 2*a* illustrates the construction of the suture device during a first stage of manufacture.
FIG. 2*b* illustrates the construction of the suture device during a further stage of manufacture.

As illustrated in FIG. 2*a*, the device 200 aptly includes a plurality of interwoven strands comprising a plurality of warp strands 250 (aligned substantially parallel with the longitudinal axis) and a plurality of weft strands 252 (aligned substantially transverse to the longitudinal axis). Aptly, the wefts are provided by a single weft strand extending through the warps. Aptly, the weft strand extends substantially perpendicularly back and forth across the device with respect to a longitudinal axis thereof and partially along an edge portion of the device substantially parallel with the longitudinal axis of the device, as illustrated. Aptly, the weft strand is thicker than a warp strand. Aptly, the weft is substantially hollow. Aptly, the warps are arranged in adjacent pairs and are interwoven with the weft strand to create a leno-weave construction (also known as a gauze weave or cross weave). Aptly, the strands include twisted fibers.

FIG. 2*b* shows an embodiment with loose strands at at least one of the ends. Either one end or both ends may have loose strands including loose warps and/or loose wefts. At least one weft strand may be essentially parallel with the warp strands, but may not be wrapped around the warp strands and/or twisted with the warp strands. As illustrated in FIG. 2*b*, a body region 202 and at least one end region 204 may be created by pulling the weft strand 252 out of the construction to create a run. The run may be pulled until the weft binds and locks to the warp strands 250 which draws the warp strands towards the central longitudinal axis of the device and creates a tapered transition region 208 between the body region 202 and the at least one end region 204. Loose strands at the ends of the at least one end region 204 may be aptly coated with a wax, silicone, PTFE, adhesive, or the like to bind them together. Desirably, the first and second end regions may be one part with the body region to provide a continuous suture device. The end region may include an unraveled body section which may further include loose warps (free ends of the warp strands) and the loose weft, where the weft resides in a longitudinal direction. This resulting structure can then be remodeled to create an end region by various means. This may include coating/gluing these loose longitudinal warp and weft strands together. A further example may include splicing the loose warp strands into the loose longitudinal weft, although this second process is only viable if the weft has a hollow, tubular, structure. This tubular structure could still be equally provided by either a braid, knit or weave.

Figure 3:
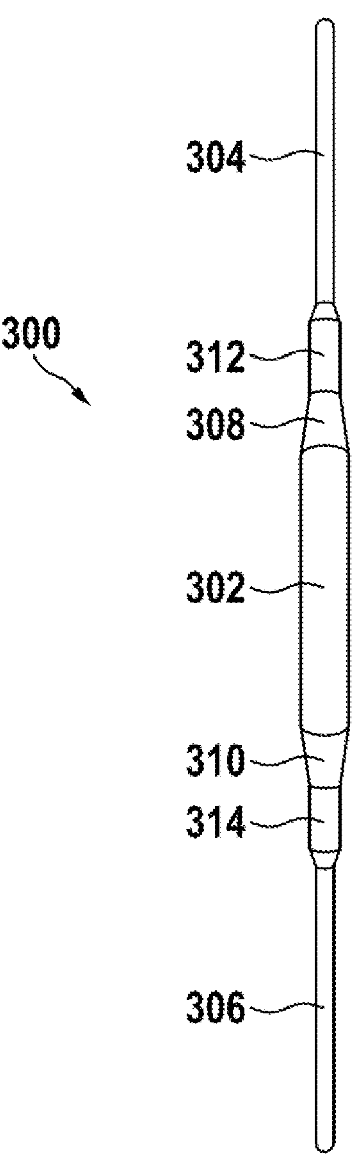
FIG. 3 illustrates a further suture.

As illustrated in FIG. 3, a surgical suture system 300 according to an embodiment includes a continuous length of suture material. The body region 302 includes a textile construction, aptly a leno-weave construction, having a plurality of warps and one or more wefts, the weft/s preferably comprising a corded construction. The weft cord is provided by interwoven strands of a knitted, braided or woven construction. Aptly, the weft cord is a braided construction with a round hollow profile. Preferably, the strands include twisted fibers. Preferably the weft cord changes orientation as it extends along the device from one region to the adjacent region. For example, as illustrated, the cord extends back and forth across the device (substantially perpendicularly to the longitudinal axis) and extends for a relatively shorter distance along an edge portion of the device and substantially parallel with the longitudinal axis. The weft cord may include a flat (or tube) woven construction (as opposed to a flat, densely packed braid) for the wider body region, where a weave is formed from the multiple warps which are positioned parallel to the long axis of the device, that are intertwined by one or more wefts which run at substantially 90 degrees to the longitudinal axis. The weft has a relatively wide cross section compared to the warp strands and is also a hollow tube to act as a hollow suture.

The tapered transition 308 located between the body region 302 and the end region 304 is created by pulling the weft cord (i.e. applying a tension to the weft cord) in substantially the longitudinal direction and out of the construction to provide a run which locks the warp strands and draws them towards the central axis. The weft cord is oriented substantially parallel with the warp strands. Loose strands adjacent to the taper are aptly placed inside the longitudinally orientated hollow weft cord via a single or series of splices, residing throughout the inside of the length of the end regions 304, 306, or terminating at a distance from the ends.

The regions 312 and 314 are the weft cord after being repositioned into the warp direction. The free ends of the mesh of body region 302 are then pulled inside this hollow tubular weft cord. As illustrated in FIG. 3, this mesh material travels inside the cord for a short distance, i.e. between the taper 310 at the end of the body region 302 and the start of the end region 306, which may be relatively thin. As such, the end region 306 is the same weft cord, whilst it does not have any of the mesh construction inside it.

The run causes the weft cord to lock the warps at the taper whilst providing the taper itself. This arrangement also allows for easier splicing, provides a smooth tapered transition from the body region 302 to the end region 306 which allows for easy passage through tissue, and provides a thin dense cord end for ease of threading through surgical instruments and creating a fixation mechanism.

According to an alternative embodiment, the surgical device may include an open mesh construction which allows a relatively wide profile to be created from a similar quantity of material. This provides an increased footprint to enhance engagement with adjacent tissue and also facilitates tissue ingrowth and postsurgical repair.

Figure 4:
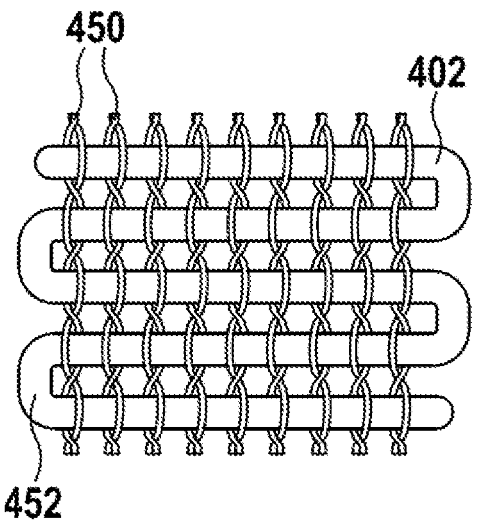
FIG. 4 illustrates the construction of the body region of a first suture.

As illustrated in FIG. 4, the body region 402 may include an open mesh construction with similar or equal spaced pairs of warp strands 450 to create a Leno-Weave construction. The warp strands 450 interweave with the weft strand 452. A leno construction is different to a woven construction (although it is described by the same terminology, warp and weft). The primary difference is that adjacent warp strands 450 (longitudinal placement) are twisted around each other in the region between consecutive single weft strands 452 (transverse placement) which may form a spiral pair or a series of figure eights, effectively 'locking' each weft strand 452 in place. Wherein the first warp strand of the spiral pair always passes under the weft strand 452 and over the second warp strand, and the second warp strand always passes over the weft strand 452. In contrast thereto, the warp strands in woven constructions do not twist around each other and resemble a linear orientation, wherein each warp strand passes both under and over successive weft strands. However, in order to achieve the desired strength for some applications, a high number of warp strands or relatively large warp strands may be provided per unit width of the fabric which reduces the pore size and in turn may compromise tissue incorporation.

Figure 5:
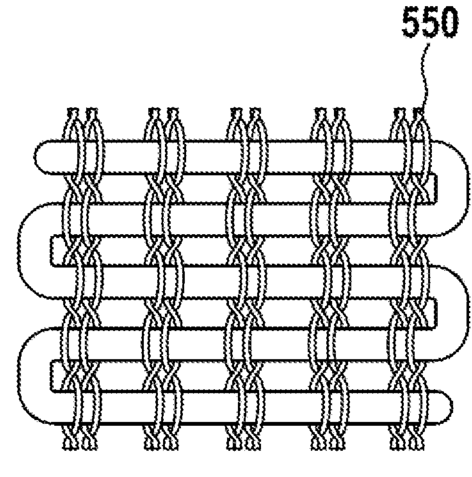
FIG. 5 illustrates the construction of the body region of a second suture.

As illustrated in FIG. 5, two or more spaced apart sets of adjacent pairs of warp strands 550 are provided which allows more strands to be incorporated per width of the fabric to thereby increase the strength thereof, whilst also enabling the pore size to be increased and optimized for tissue incorporation.

Figure 6:
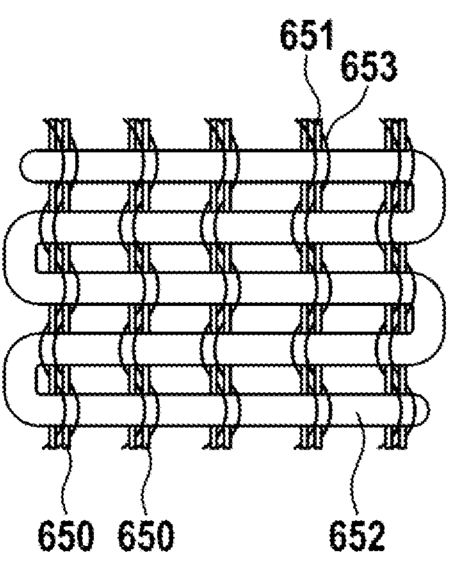
FIG. 6 illustrates the construction of the body region of a third suture.

As illustrated in FIG. 6, two or more spaced apart sets of adjacent pairs of warp strands 650 are provided wherein a pair includes a 'parallel' strand 651. For example, one strand 651 from a warp pair is placed 'parallel' (substantially planar) in the fabric while the other strand 653 of the warp pair interweaves with the weft strand 652 to thereby bind the parallel warp strands and the weft strand. The parallel warp strands take the majority of the applied axial load and, due to their parallel orientation, the construction provides increased resistance to elongation when placed under an axial load.

Figure 7:
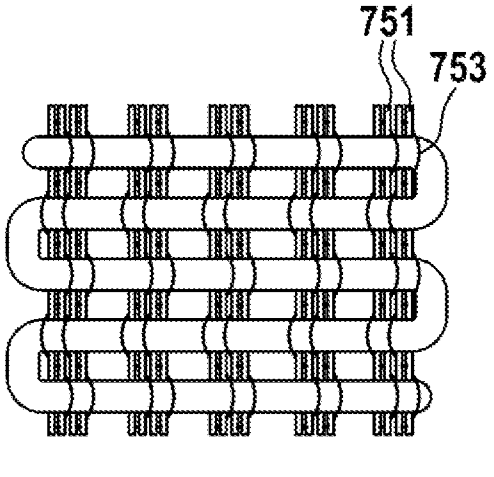
FIG. 7 illustrates the construction of the body region of a fourth suture.

Aptly, as illustrated in FIG. 7, the construction may incorporate a greater number of parallel warp strands 751 than the 'binding' warp strands 753. This construction may be desirable in situations where increased stiffness of the fabric may be provided.

Preferably, the parallel warp strands 751 have a larger diameter than the binding warp strands 753. This allows a particularly desirable fabric to be created having a relatively high strength (greater number of warps), relatively high stiffness (parallel warps), and optimum pore size for tissue incorporation.

Figure 14A:
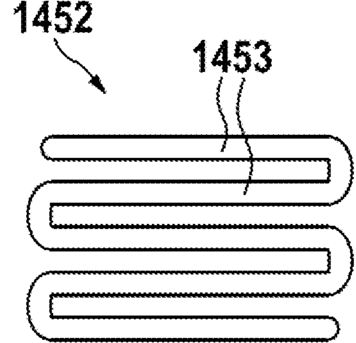
FIGS. 14*a* to 14*c* illustrate the construction of the body region of a further suture.
Figure 14B:
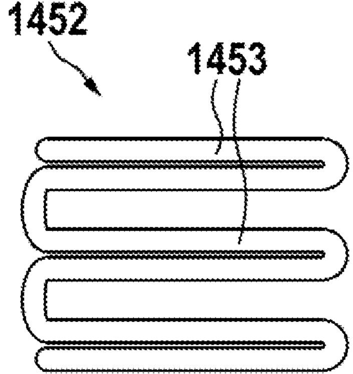
Figure 14C:
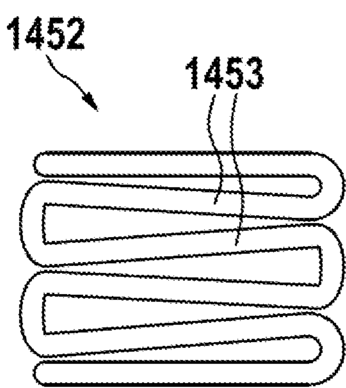

Alternatively, one or more binding warp strands may have a similar, larger or smaller diameter to the other strands. One or more parallel warp strands may have a similar, larger or smaller diameter to the other strands. One or more weft strands may have a similar, larger or smaller diameter to the other strands. One or more warp and/or weft strands may be equally or not equally spaced. For example, as illustrated in FIG. 14*a*, the transverse portions 1453 of the weft strand 1452 may be substantially parallel and equally spaced relative to the other. Alternatively, as illustrated in FIG. 14*b*, the transverse portions 1453 of the weft strand 1452 may be substantially parallel with the other but not equally spaced relative to the other. Further alternatively, as illustrated in FIG. 14*c*, the transverse portions 1453 of the weft strand 1452 may not be parallel to the other.

According to an alternative embodiment, the body region of the device may include an open mesh construction and the at least one end region may be of a thinner construction to facilitate threading through tissue and eyelets in surgical instruments. The thinner end region/s may be formed by a series of tapers, binding and/or splicing, as previously described.

Figure 8:
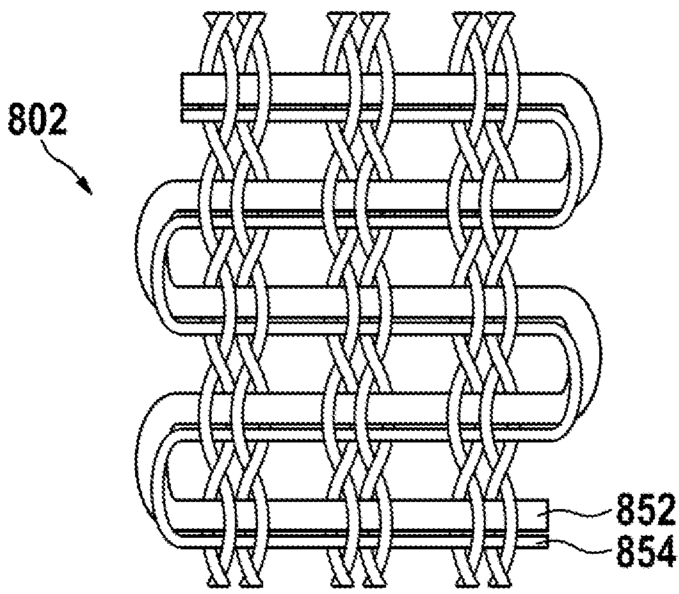
FIG. 8 illustrates the construction of the body region of a fifth suture.

As illustrated in FIG. 8, the body region 802 of the device according to an alternative embodiment may include an open mesh construction comprising a plurality of weft strands 852, 854 to create the leno-weave construction. This provides the ability for different constructions along the length of the device.

Figure 9:
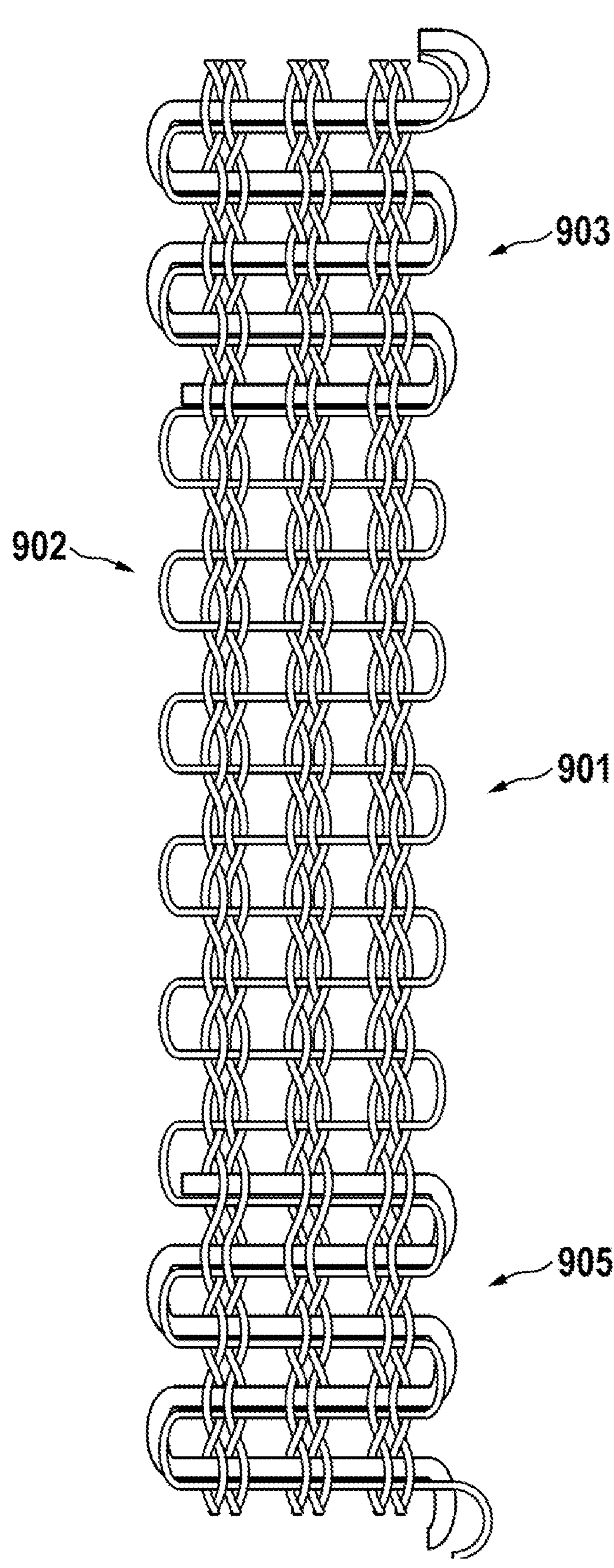
FIG. 9 illustrates the construction of the body region of a sixth suture.

As illustrated in FIG. 9, portions of the body region 902 may have more or less weft yarns than adjacent portions. For example, the end portions 903,905 of the body region may have multiple weft strands, while a central portion 901 of the body region may have less weft strands. This provides a central portion 901 of the body region having an optimized construction for tissue incorporation and end body portions 903,905 having a construction for optimized coupling with bone, soft tissue, fixation devices, or the like. Alternatively, the central portion 901 has more weft strands than the adjacent end portions 903,905.

Figures 10A, 10B, 10C:
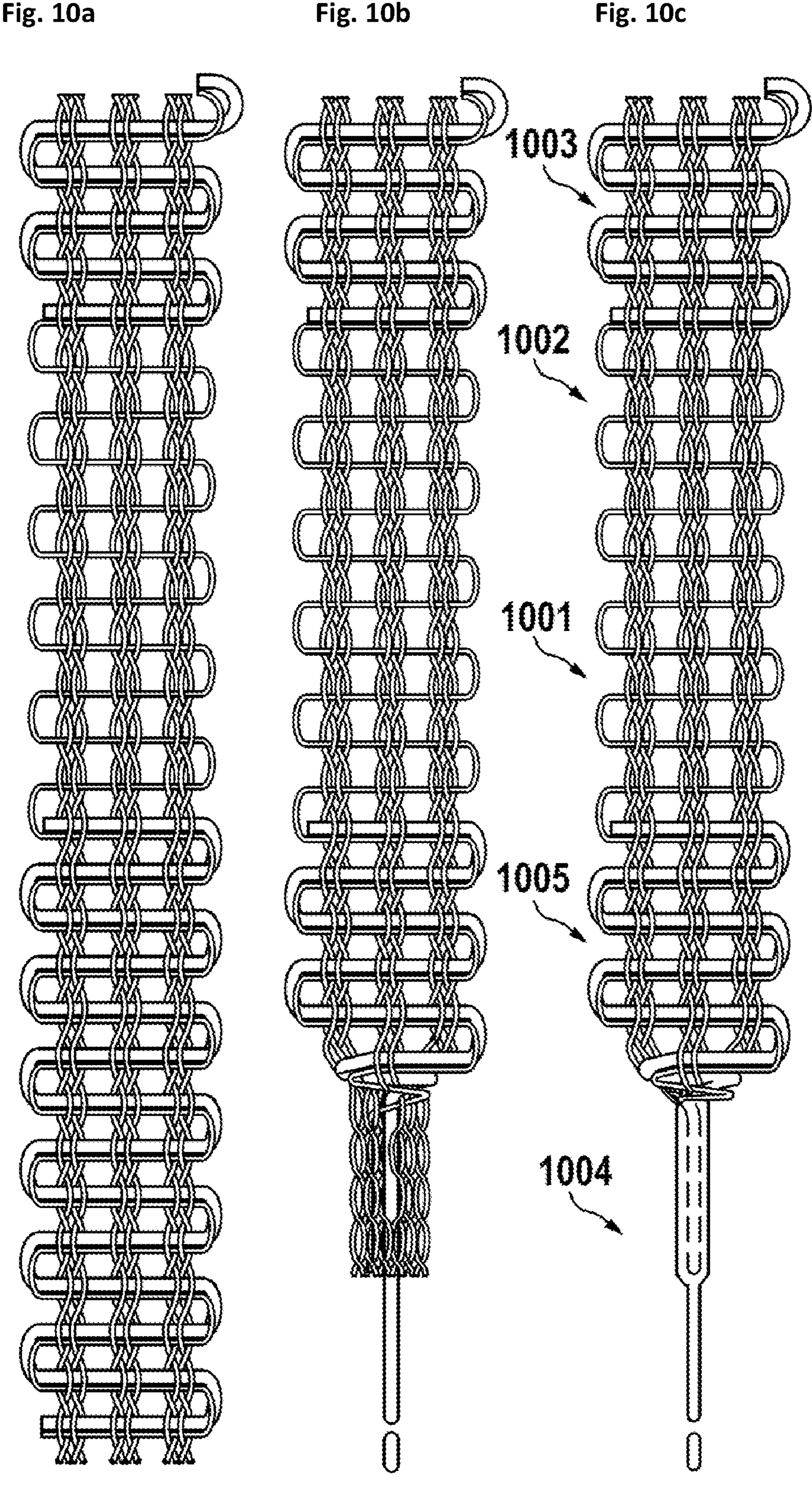
FIG. 10*a* illustrates the construction of a seventh suture during a first stage of manufacture.
FIG. 10*b* illustrates the construction of the seventh suture during a further stage of manufacture.
FIG. 10*c* illustrates the construction of the seventh suture during a further stage of manufacture.

According to an alternative embodiment, as illustrated in FIGS. 10*a* to 10*c*, one or more wefts in one or both end portions of the body region 1002 may include a braided cord into which the warps and further weft/s can be spliced to form an end region 1004. The other weft strands, together with the warp strands are formed from filaments, which provides a soft and pliable middle portion 1001 of body region 1002 for enhanced tissue ingrowth, while the end portions 1003,1005 of the body region 1002 have an optimized construction to aid fixation and create the transition to the end cord.

Figures 11A, 11B:
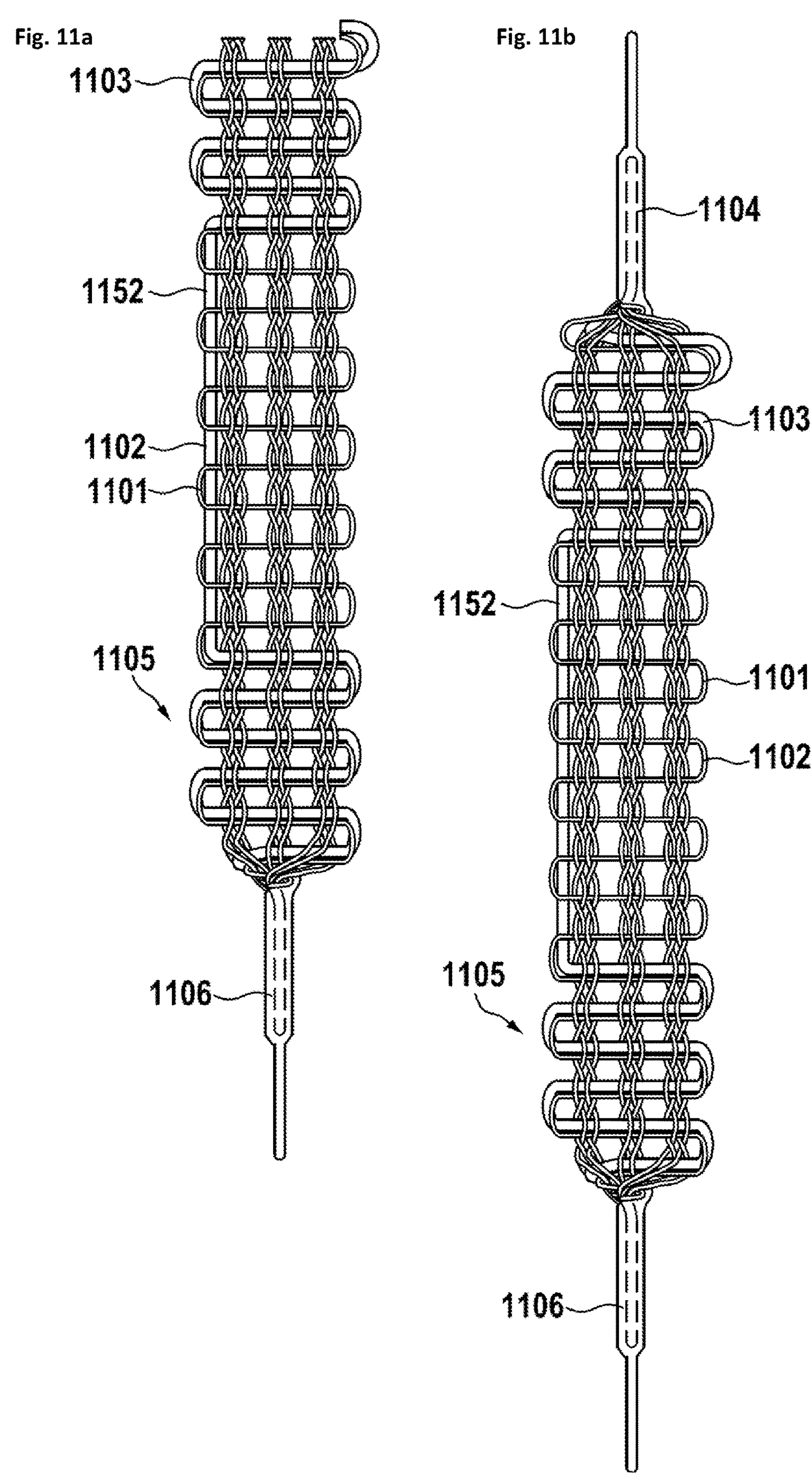
FIG. 11*a* illustrates the construction of an eighth suture.
FIG. 11*b* illustrates the construction of a ninth suture.

According to an alternative embodiment, the wefts in the end portions 1103,1105 of the body region 1102 are continuous, with one or more wefts 1152 running at least partially along the edge of a central portion 1101 the body region and substantially parallel to the longitudinal axis. This arrangement provides a soft and pliable middle portion to the body region 1102 for enhanced tissue ingrowth, while the edge portions of the body region have increased strength provided by the second weft. FIG. 11*a* illustrates a device having with one end region 1106, and FIG. 11*b* illustrates a device having two end regions 1104,1106.

Figure 12D:
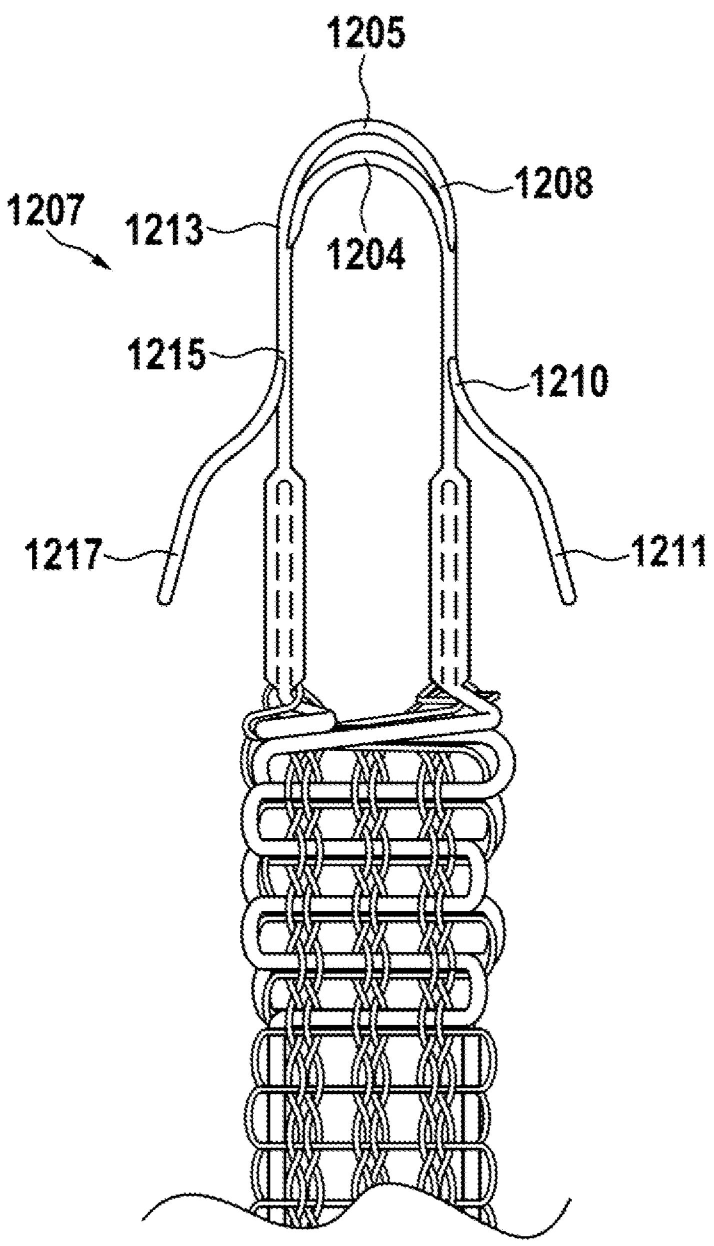
FIG. 12*d* illustrates the construction of a thirteenth suture.

According to an alternative embodiment, multiple sets of wefts may be used. In a first example, as illustrated in FIG. 12*a*, a first cord end 1260 is spliced inside a second cord end 1262 together with the remaining wefts and warps to provide a single end region 1204. In a second example, as illustrated in FIG. 12*b*, a weft cord is a discrete end to provide a pair of spaced apart end portions 1204,1205 extending from at least one end region of the device. In a third example, as illustrated in FIG. 12*c*, a weft cord is a discrete end which are then spliced together to form a loop 1206. In a fourth example, as illustrated in FIG. 12*d*, a weft cord is a discrete end which are then spliced to form an adjustable length loop 1207. This arrangement provides a fixation mechanism to allow the device to be attached to tissue. For example, the adjustable length loop may be formed by a weft cord penetrating the suture wall of the opposing weft.

Weft 1204 penetrates opposing weft 1205, entering at point 1208 and residing along the interior lumen of the opposing weft 1205, and exiting the weft 1205 at point 1210 thereby creating a loop which is adjustable in length when free end of cord 1211 is pulled, and locked in length when the loop 1207 is under load. Similarly, weft 1205 penetrates opposing weft 1204 at point 1213, passes within weft 1204, and exits weft 1204 at point 1215 to create free end of cord 1217. Alternatively, any weft cord may form a discrete adjustable loop by passing within itself. Alternatively, a button may be attached to one or more loops to aid fixation.

Figures 13A, 13B, 13C:
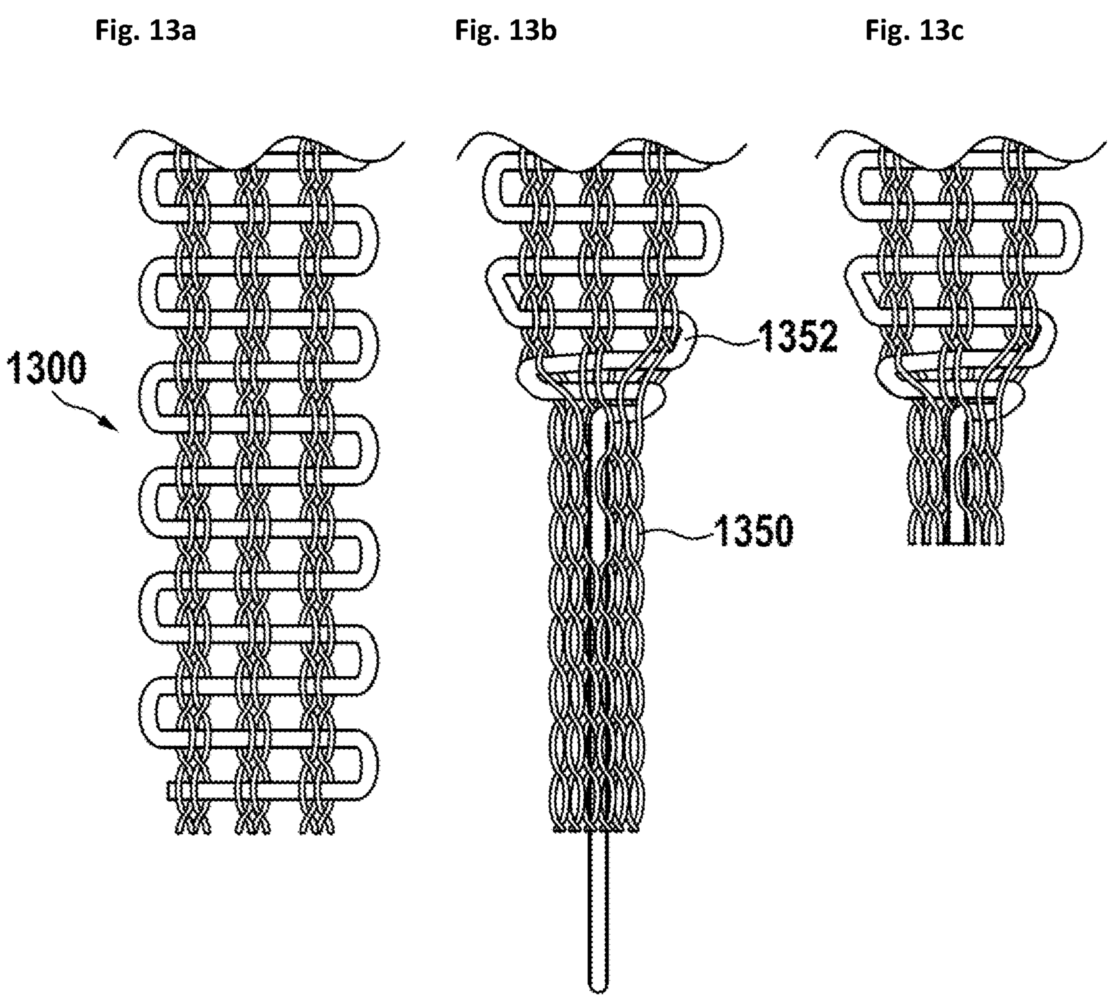
FIGS. 13*a* to 13*c* illustrate a method of manufacturing a suture.

According to an alternative embodiment, the device is aptly configured to facilitate cutting away surplus material following implantation. Typically, such open mesh constructions are unstable when cut to length, with the strands at the end of the device fraying and splaying with the textile construction becoming unraveled. A method is described by which the device 1300 is cut to a first length (FIG. 13*a*), a run is created by pulling the weft strand 1352 until the weft binds and locks to the warp strands 1350 (FIG. 13*b*), the device may then be cut to a second length that is shorter than the first length whist retaining the bound strands (FIG. 13*c*). This creates a stable end to the device which would not further unravel past the bind. Aptly, the spacing between adjacent passes of the weft strand are set to facilitate this action. By way of example, if the run takes 16 mm of length to be pulled before binding and if adjacent weft passes are spaced 2 mm, when the bind may be located at a particular position (for example adjacent to a knot), counting back 8 weft passes from the desired location and making the first cut to length will then position the bind at the desired location. Aptly, the weft has a larger diameter than the warps, and is formed from a braided construction and has a different color to the warps, so that it is easily identifiable to facilitate this method.

Figure 15A:
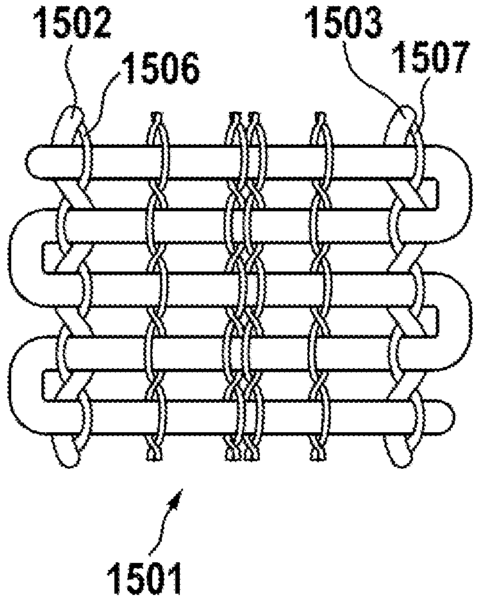
FIGS. 15*a* to 15*b* illustrate a further embodiment with modified warp cords.
Figure 15B:
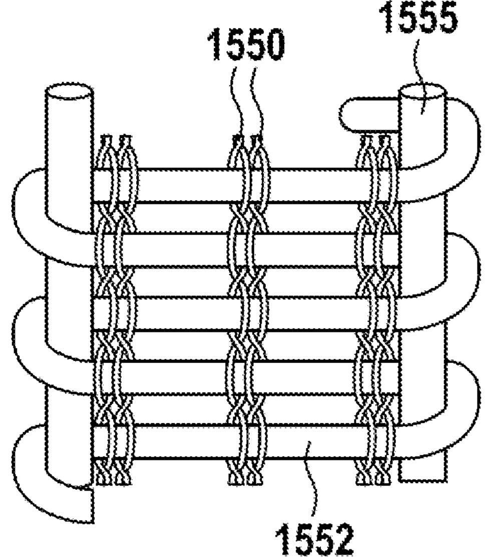

According to an alternative embodiment, one or more warp cords may be used. In a first example, as illustrated in FIG. 15*a*, a first warp cord 1502 runs along the edge of a central portion 1501 of the body region and substantially parallel to the longitudinal axis. A second warp cord 1503 runs along the opposite edge of a central portion 1501 of the body region. A warp cord 1502, 1503 is paired with a warp strand 1506, 1507 to bind the warp cord to the body region. This arrangement provides a soft and pliable middle portion to the body region 1501 for enhanced tissue ingrowth, while the edge portions of the body region have increased strength provided by the warp cord. In a second example, as illustrated in FIG. 15*b*, each warp cord 1555 is bound to the body region by one or more weft strands 1552 and adjacent pairs of warp strands 1550. Preferably end portions extending from at least one end region of the device are formed by splicing warp cords and warp filaments into one or more wefts which may include a braided cord. According to an embodiment, end portions extending from at least one end region of the device are formed by splicing wefts and warp filaments into one or more warp cords. According to an embodiment, end portions extending from at least one end region of the device are formed by splicing weft cords, warp cords and warp filaments.

Figure 16A:
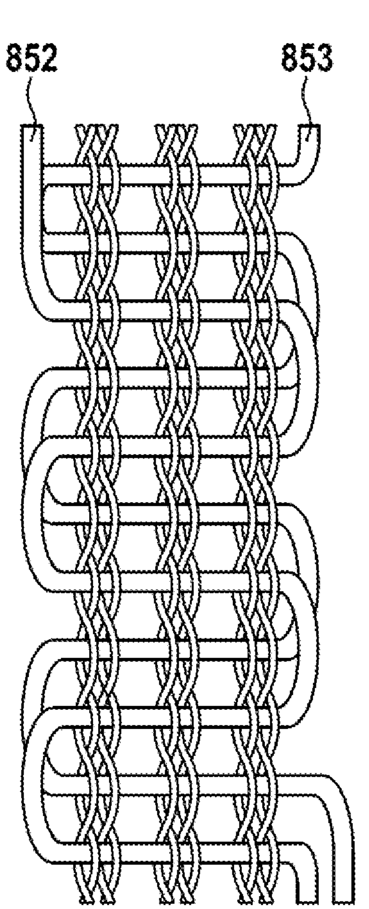
FIGS. 16*a* to 16*b* illustrate a further embodiment.
Figure 16B:
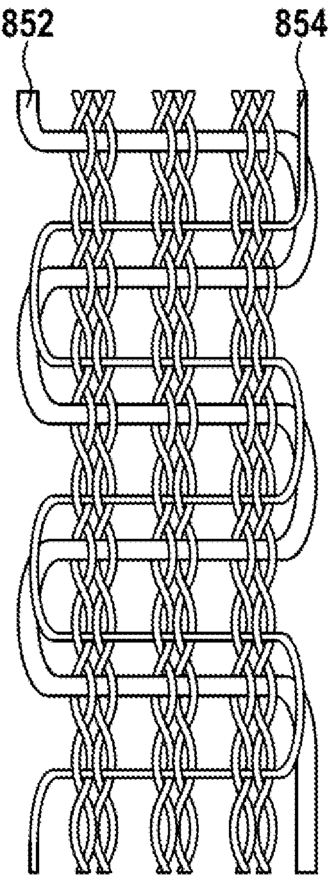

In FIGS. 16*a* and 16*b* further embodiments are shown. Whereas in the embodiment of FIG. 8, two weft strands pass through the same twist created by a pair of warp strands, here each of the two weft strands may be bounded by a separate twist. More weft strands may be either be bounded by the same twists or by different twists. The weft strands may include a yarn and/or a braid. In FIG. 16*a* an embodiment with two similar weft strands 852, 853 is shown. FIG. 16*b* shows an embodiment with different types of weft strands 852, 854.

The construction of any region of the device in regards to width, length, cross sectional shape, density, pore size, material type and mechanical properties may be adapted for its function, whereby the mechanical properties may include one or a combination of; strength, stiffness, wettability, flexibility and rate of absorption, and any region may have, for example, a variance in any one or a combination of the above mentioned physical or mechanical properties. Variations in the properties of the warp or weft strands may be substantially equally or unequally spaced relative to one another. One or more of the warp strands may include a different cross-sectional size to other warp strands. The warp strands may be equal to, greater than and/or smaller than the denier of the weft strands. The body region of the device may have undulations in the surface to provide increased frictional resistance to aid knot tying. One or more of the warp strands may include a larger cross-sectional area to create one or more ridges. One or more of the weft strands may include a larger cross-sectional area to create one or more ridges. The body region may be planer or tubular in cross section.

The suture material may include a single or a blend of materials. The materials that create the textile fabric may include bioabsorbable or non-bioabsorbable substances from natural or artificial sources including for example, gut, silk, cotton, ultra-high molecular weight polyethylene (UHMWPE) polyamide (Nylon), polyethylene terephthalate (PET), polyethylene (PE), polypropylene (PP), polydioxanone polyetheretherketone (PEEK), polyetherketoneketone (PEKK), graphene, or bioabsorbable materials whether as a single material or as a blend of materials. A combination of ultra-high molecular weight polyethylene (UHMWPE) and polyethylene terephthalate (PET) may be used to provide strength and improved knotting characteristics respectively. Pairs of warp strands may be used where one of the strands is UHMWPE and one PET. Preferably the UHMWPE has a larger cross-sectional area, in effect a greater denier, and is substantially parallel to transmit the load, where the smaller denier PET strand acts to bind the UHMWPE strand to the weft strands. Colored strands may be incorporated to enhance visibility during use. Colored strands are aptly fashioned from dyed fibres of UHMWPE, PET or nylon. Different colors or patterns of color may be used in different regions for identification.

Embodiments provide a suture device that provides improved utility for a range of surgical applications, whilst allowing the device to be used with existing surgical instrumentation. The device is configured to improve pressure distribution to adjacent tissue during and after a surgical repair and to reduce/eliminate any undesirable contact forces which could result in cutting of the adjacent tissue. The device is configured to provide improved strength and optimized coupling with bone, soft tissue or fixation devices. The device includes a relatively wide and open mesh main body region to create a large footprint resistant to tissue pull-through and to encourage tissue interaction. The relatively thin end regions are adapted to pass through relatively small eyelets in standard surgical instruments to facilitate efficient transit through tissue during surgical procedures.

Figure 17A:
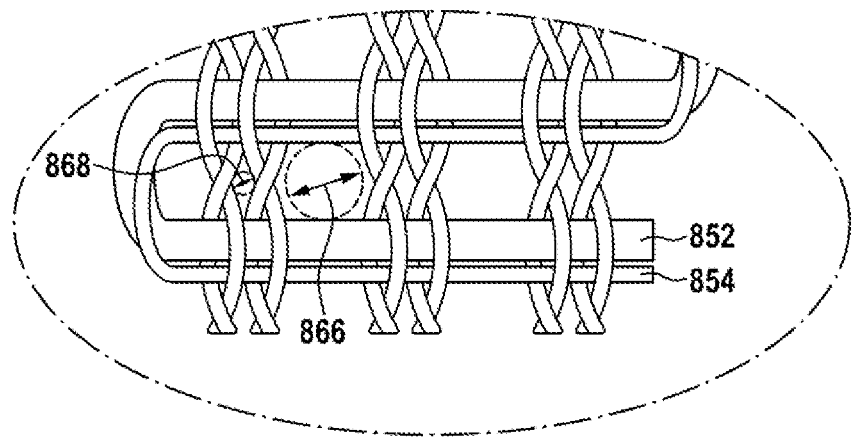
FIGS. 17*a* and 17*b* show schematically, how pore sizes may be defined.
Figure 17B:
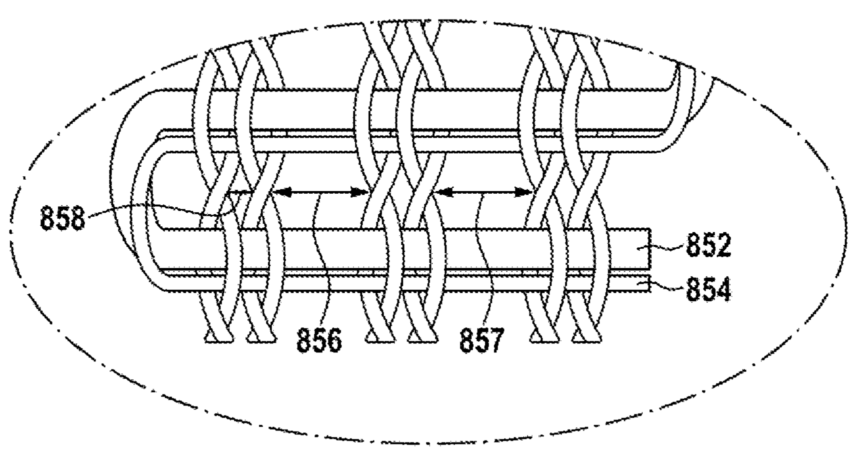

FIGS. 17*a* and 17*b* show schematically, how pore sizes may be defined. A section of the embodiment of FIG. 8 is used as an example, but the definition of pore size may be applied to any embodiment disclosed herein.

A preferred definition is as shown in FIG. 17*a*, by the diameter of a circle superimposed within the void between adjacent strands. An open pore has a circle with diameter 866 which may be more than 100 μm. A closed pore has a circle with diameter 868 which may be less than 100 μm. Generally, an open pore has a larger circle than a closed pore.

If the weft strands have a distance larger than the warp strands, then the diameter of the circle is mainly determined by the distance of the warp strands. This is shown in FIG. 17*b*. The distance 858 of the smaller gap between wefts is approximately the same as the smaller circle 868. Further the distance of the larger gaps 856 and 857 is approximately the same as the larger circle 866. Accordingly, the distance between adjacent wefts may be used as a simplified measure of pore size.

The invention claimed is:

1. A suture device (100) comprising:

a body region (102) including at least one weft strand (252) interwoven with a plurality of warp strands (250) in a leno weave, wherein the at least one weft strand (252) has a thickness larger than each of the plurality of warp strands (250); and at least one elongate end region (104) axially extending from and being one part with the body region (102) and having a width less than a width of the body region (102), wherein the at least one weft strand (252) interwoven with the plurality of warp strands (250) define a first region of the body region (102) having an open mesh construction and at least a first elongate region of the at least one elongate end region (104) axially extending from and being one part with the body region (102) wherein the at least first elongate region has a closed mesh construction and a width less than a width of the body region (102), and wherein the at least one elongate end region (104) comprises at least one of the at least one weft strand (252), wherein at least one end portion of the body region (102) comprises at least one of the at least one weft strand (252), and wherein the at least one of the at least one weft strand (252) of the at least one end portion of the body region (102) is stiffer than at least one of the at least one weft strand (252) of a central portion of the body region (102), and wherein the at least one of the at least one weft strand (252) of the central portion of the body region (102) comprises at least one filament.

2. The suture device (100) according to claim 1, wherein the open mesh construction has an average pore size of more than 100 μm, and the closed mesh construction has an average pore size of less than 100 μm.

3. The suture device (100) according to claim 1 wherein the leno weave includes at least a first and a second warp strand twisted in a series of figure eights around at least one weft strand, wherein the first warp strand passes under the weft strand and over the second warp strand and the second warp strand passes over the weft strand.

4. The suture device (100) according to claim 1, wherein a second elongate end region (106) axially extends from the body region (102) and is provided in an opposed direction to the first elongate end region (104) and is one part with the body region (102) and the at least one elongate end region (104) has no undulations and has a constant width.

5. The suture device (100) according to claim 1, wherein the plurality of warp strands (250) comprises sets of at least two warp strands (250), wherein any set of warp strands (250) comprises groups of adjacent pairs of warp strands (250) and the sets of warp strands (250) of the body region (102) are parallel and spaced apart.

6. The suture device (100) according to claim 1, wherein a first warp strand (250) of a set of warp strands (250) is planar and a second warp strand (250) of a set is interwoven with the at least one weft strand (252), and any set of warp strands (250) comprises a greater number of said first warp strands (250) than said second warp strands (250) and a thickness of said first warp strand (250) is greater than a thickness of said second warp strand.

7. The suture device (100) according to claim 1, wherein the central portion of the body region (102) comprises a single weft strand (252).

8. The suture device (100) according to claim 7, wherein the stiffer weft strands (252) comprises a braided cord.

9. The suture device (100) according to claim 7, wherein a first weft strand (252) of the plurality of weft strands (252) is thicker than a second weft strand (252) of the plurality of weft strands (252).

10. The suture device (100) according to claim 9, wherein the at least one weft strand (252) extends longitudinally from a portion of the body region (102) and wherein the at least one weft strand (252) extends along at least one edge of a central portion of the body region (102), and wherein the at least one weft strand (252) extends along opposed edges of a central portion of the body region (102) and wherein the at least one weft strand (252) of the at least one end region (104, 106) comprises at least one corded construction.

11. The suture device (100) according to claim 10, wherein at least an end portion of the at least one corded construction is hollow and wherein free ends of the warp strands (250) of the at least one end region (104, 106) may be located inside the at least one corded construction by one or more splices to define at least one corded end region (104, 106).

12. A method of manufacturing the suture device of claim 1, comprising:

interweaving at least one weft strand (252) with a plurality of warp strands (250) to define an open mesh construction; and applying a tension to the at least one weft strand (252) to urge the warp strands (250) together and define a body region (102) having an open mesh construction and at least a first elongate end region (104, 106) axially extending from and being one part with the body region (102) having a closed mesh construction and a width less than a width of the body portion.

13. A suture device (100) comprising:

a body region (102) including at least one weft strand (252) interwoven with a plurality of warp strands (250)

in a leno weave, wherein the at least one weft strand (252) has a thickness larger than each of the plurality of warp strands (250); and at least one elongate end region (104) axially extending from and being one part with the body region (102) and having a width less than a width of the body region (102), wherein an average pore size of the body region (102) is larger than an average pore size of the at least one elongate end region (104), and wherein at least one end portion of the body region (102) comprises at least one of the at least one weft strands (252), and wherein the at least one of the at least one weft strand (252) of the at least one end portion of the body region (102) is stiffer than at least one of the at least one weft strand (252) of a central portion of the body region (102), and wherein the at least one of the at least one weft strand (252) of the central portion of the body region (102) comprises at least one filament.

14. The suture device (100) according to claim 13, wherein the average pore size of the body region (102) is at least 100 μm and the average pore size of the at least one elongate end region (104) is less than 100 μm.

* * * * *